US009400214B1

(12) United States Patent
Demers et al.

(10) Patent No.: US 9,400,214 B1
(45) Date of Patent: Jul. 26, 2016

(54) TERAHERTZ FREQUENCY DOMAIN SPECTROMETER WITH A SINGLE PHOTOCONDUCTIVE ELEMENT FOR TERAHERTZ SIGNAL GENERATION AND DETECTION

(71) Applicant: Joseph R. Demers, Pasadena, CA (US)

(72) Inventors: Joseph R. Demers, Pasadena, CA (US); Ronald T. Logan, Jr., Pasadena, CA (US); Bryon Kasper, Sierra Madre, CA (US)

(73) Assignee: Joseph R. Demers, Pasadena, CA (US)

( * ) Notice: Subject to any disclaimer, the term of this patent is extended or adjusted under 35 U.S.C. 154(b) by 16 days.

(21) Appl. No.: 14/183,088

(22) Filed: Feb. 18, 2014

Related U.S. Application Data

(60) Provisional application No. 61/790,973, filed on Mar. 15, 2013.

(51) Int. Cl.
| G01J 5/02 | (2006.01) |
| G01J 3/28 | (2006.01) |
| G01J 3/42 | (2006.01) |
| G01J 3/02 | (2006.01) |
| G01J 3/10 | (2006.01) |
| G01N 21/3581 | (2014.01) |
| G01N 21/3586 | (2014.01) |

(52) U.S. Cl.
CPC .............. *G01J 3/42* (2013.01); *G01J 3/0256* (2013.01); *G01J 3/10* (2013.01); *G01N 21/3581* (2013.01); *G01N 21/3586* (2013.01)

(58) Field of Classification Search
CPC ... G01N 21/3581; G01N 21/3586; G01J 3/42; G01J 3/10; G01J 3/0256
USPC ........................................ 250/339.06, 339.07
See application file for complete search history.

(56) References Cited

U.S. PATENT DOCUMENTS

| 4,594,511 A | 6/1986 | Cooper et al. |
| 5,379,110 A | 1/1995 | Matsui et al. |

(Continued)

FOREIGN PATENT DOCUMENTS

| EP | 1233527 | 8/2002 |
| GB | 2381121 | 4/2003 |
| GB | 2483118 | 2/2012 |
| WO | WO 2007/135382 A2 | 11/2007 |
| WO | WO 2009/082820 A1 | 7/2009 |
| WO | WO 2009/137263 A2 | 11/2009 |

(Continued)

OTHER PUBLICATIONS

U.S. Appl. No. 14/212,542, filed Mar. 14, 2014, Demers et al.

(Continued)

*Primary Examiner* — David Porta
*Assistant Examiner* — Abra Fein
(74) *Attorney, Agent, or Firm* — Pritzkau Patent Group, LLC

(57) ABSTRACT

There is described an apparatus for analyzing, identifying or imaging a target. The apparatus comprises a laser system which generates first and second laser beams having respective different frequencies, and directs the first and second laser beams along an optical path to a photoconductive material. An antenna structure is formed on the photoconductive material, the antenna structure comprises a first antenna for emitting electromagnetic radiation having a frequency dependent on the difference between said respective different frequencies of the first and second laser beams and a second antenna for generating a detection signal. A processor processes the detection signal to analyze, identify or image the target. The laser system is arranged such that the first and second laser beams overlap in a region of a surface of the photoconductive material having at least part of the first and second antennas formed thereon.

24 Claims, 6 Drawing Sheets

(56) References Cited

U.S. PATENT DOCUMENTS

| | | | |
|---|---|---|---|
| 5,379,309 | A | 1/1995 | Logan, Jr. |
| 5,623,145 | A | 4/1997 | Nuss |
| 6,304,219 | B1 | 10/2001 | Rothe et al. |
| 6,348,683 | B1 | 2/2002 | Verghese et al. |
| 6,434,496 | B1 | 8/2002 | Dong et al. |
| 6,545,785 | B1 | 4/2003 | Heflinger et al. |
| 6,811,552 | B2 | 11/2004 | Weil, Sr. et al. |
| 6,816,647 | B1 | 11/2004 | Rudd et al. |
| 6,828,558 | B1 | 12/2004 | Arnone et al. |
| 6,844,552 | B2 | 1/2005 | Zhang et al. |
| 6,849,852 | B2 | 2/2005 | Williamson |
| 6,865,014 | B2 | 3/2005 | Ciesla et al. |
| 6,957,099 | B1 | 10/2005 | Arnone et al. |
| 7,126,078 | B2 | 10/2006 | Demers et al. |
| 7,174,037 | B2 | 2/2007 | Arnone et al. |
| 7,244,934 | B2 | 7/2007 | Arnone et al. |
| 7,291,835 | B2 | 11/2007 | Overney |
| 7,291,839 | B1 | 11/2007 | Demers et al. |
| 7,335,883 | B2 | 2/2008 | Wallace et al. |
| 7,439,511 | B2 | 10/2008 | Demers |
| 7,485,863 | B2 | 2/2009 | Cole |
| 7,535,005 | B2 | 5/2009 | Demers |
| 7,781,736 | B2 | 8/2010 | Logan, Jr. et al. |
| 7,804,069 | B2 | 9/2010 | Tribe |
| 7,936,453 | B2 | 5/2011 | Logan, Jr. et al. |
| 7,963,571 | B2 | 6/2011 | Martin |
| 8,138,477 | B2 | 3/2012 | Gregory |
| 8,604,433 | B2 | 12/2013 | Logan, Jr. et al. |
| 8,829,440 | B2 | 9/2014 | Logan, Jr. et al. |
| 2003/0155512 | A1 | 8/2003 | Arnone et al. |
| 2004/0065831 | A1 | 4/2004 | Federici et al. |
| 2005/0030377 | A1* | 2/2005 | Li .............................. 348/143 |
| 2005/0162658 | A1 | 7/2005 | Pepper |
| 2006/0084180 | A1 | 4/2006 | Paldus et al. |
| 2006/0214107 | A1 | 9/2006 | Mueller |
| 2006/0255277 | A1 | 11/2006 | Cole et al. |
| 2008/0159418 | A1* | 7/2008 | Anderson et al. ............. 375/260 |
| 2008/0179519 | A1 | 7/2008 | Andonian et al. |
| 2008/0179528 | A1 | 7/2008 | Demers |
| 2008/0212974 | A1 | 9/2008 | Davies et al. |
| 2008/0251720 | A1 | 10/2008 | Xu et al. |
| 2009/0015714 | A1* | 1/2009 | Hendrix et al. ............... 348/484 |
| 2009/0015843 | A1 | 1/2009 | Demers et al. |
| 2009/0066948 | A1 | 3/2009 | Karpowicz et al. |
| 2009/0091820 | A1 | 4/2009 | McCarthy et al. |
| 2009/0180122 | A1 | 7/2009 | Federici |
| 2009/0200472 | A1 | 8/2009 | Gregory |
| 2009/0283680 | A1 | 11/2009 | Logan, Jr. et al. |
| 2010/0080505 | A1 | 4/2010 | Sartorius et al. |
| 2010/0092183 | A1 | 4/2010 | Kim et al. |
| 2010/0171835 | A1 | 7/2010 | Kasai et al. |
| 2010/0314545 | A1* | 12/2010 | Logan et al. ............ 250/339.07 |
| 2011/0032955 | A1 | 2/2011 | Daiber |
| 2011/0068268 | A1 | 3/2011 | Heidari |
| 2012/0075477 | A1 | 3/2012 | Daly et al. |
| 2012/0326039 | A1 | 12/2012 | Demers et al. |
| 2013/0200263 | A1 | 8/2013 | Logan et al. |
| 2014/0021351 | A1 | 1/2014 | Logan et al. |
| 2014/0043612 | A1 | 2/2014 | Logan, Jr. et al. |

FOREIGN PATENT DOCUMENTS

| | | |
|---|---|---|
| WO | WO 2009/137263 A3 | 1/2010 |
| WO | WO 2012057710 A1 * | 5/2012 |

OTHER PUBLICATIONS

U.S. Appl. No. 14/262,249, filed Apr. 25, 2014, Demers et al.

U.S. Appl. No. 14/262,291, filed Apr. 25, 2014, Demers et al.

Arnone et al., "Applications of Terahertz (THz) Technology to Medical Imaging," *Proc. SPIE Terahertz Spectroscopy Applicat. II*, 1999; 3823:209-219.

Arnone et al., "Terahertz Imaging Comes Into View," *Phys. World*, 2000; pp. 35-40.

Bartels et al., "Femtosecond Time-Resolved Optical Pump-Probe Spectroscopy at Kilo Rates Over Nanosecond-Time-Delays Without Mechanical Delay Line," *Appl. Phys. Lett.*, 2006; 88:04117.

Bartels et al., "High-Resolution THz Spectrometer with kHz Scan Rates," *Optics Express*, 2006; 14(1):430-437.

Bjanason et al., "ErAs:GaAs Photomixer with two decades tenability and 12 μW Peak Output," *Applied Physics Letters*, 2004; 85(18):3983-3985.

Brown et al., "Characterization of a Planar Self-Complementary Square-Spiral Antenna in the THz Region," *Microwave and Optical Technology Letters*, Mar. 2006; 48(3):524-529.

Brown, "Advancements in Photomixing and Photoconductive Switching for THz Spectroscopy and Imaging," *Proc. of SPIE*, 2013; 7938:793802-1-793802-16.

Chang et al., "Power Scalable Compact THz System Based on an Ultrafast Yb-doped Fiber Amplifier," *Optics Express*, 2006; 14(17):7909-7913.

Chen et al., "Spectroscopic Applications and Frequency Locking of THz Photomixing with Distributed-Bragg-Reflector Diode Lasers in Low-Temperature-Grown GaAs," *Appl. Phys. Lett.*, 1997; 71(12):1601-1603.

Combined Search and Examination Report for Application No. GB1309663.1 dated Nov. 13, 2013; 8 pgs.

Demers et al., "An Optically Integrated Coherent Frequency-Domain THz Spectrometer with Signal-to-Noise Ratio up to 80 dB," 2007 IEEE Conference; pp. 92-95.

Demers et al., "Field-portable THz Spectrometer for Characterization of Explosives and Chemicals," IEEE IRMMW Conference, Houston, TX, Oct. 6, 2011; 26 pgs.

Gutierrez, "An Electro-Optical Frequency Shifter," NASA's Jet Propulsion Laboratory, 2000; Available at <URL:http://www.nasatech.com/Briefs/Sept00/NPO20531.html>.

Hu et al., "Imaging with Terahertz Waves," *Optics Letters*, 1995; 20(16):1716-1718.

Hunsche et al., "Terahertz 'T-Ray' Tomography," *Proc. SPIE Int. Millimeter Submillimeter Waves Applicat. IV.*, 1998; 50(3):426-433.

Intellectual Property Office Search Report for Application No. GB10170462 dated Nov. 16, 2010; 1 page.

Izutsu et al., "Integrated Optical SSB Modulator/Frequency Shifter," *IEEE Journal of Quantum Electronics*, Nov. 1981, QE-17:2225-2227.

Janke et al., "Asynchronous Optical Sampling for High-Speed Characterization of Integrated Resonant Terahertz Sensors," *Optics Letters*, 2005; 30(11):1405-1407.

Jiang et al., "Terahertz Imaging via Eletrooptic Effect," *IEEE Trans. Microwave Theory Tech.*, 1999; 47:2644-2650.

Logan, Jr. et al., "Field Portable THz Spectrometer for Characterization of Explosives and Chemicals," Emcore Corporation Conference Publication, Oct. 2011; 3 pgs.

McGrath et al., "Superconducting Hot Electron Mixers with Ultra Wide RF Bandwidth for Heterodyne Receiver Applications Up to 3 THz," *Proceedings of the ESA Symposium*, 1997; pp. 401-404.

McIntosh et al., "Terahertz Measurements of Resonant Planar Antennas Coupled to Low-Temperature-Grown GaAs Photomixers," *Appl. Phys. Lett.*, 1996; 69(24):3632-3634.

Mittleman et al., "T-Ray Imaging," *IEEE J. Select. Topics Quantum Electron*, 1996; 2:679-692.

Saleh et al., "Fundamentals of Photonics," Wiley-Interscience, 1991; pp. 719-720, 823-825.

Siegel, "Terahertz Technology," *IEEE Transactions on Microwave Theory and Techniques*, 2002; 50(3):915-917.

Verghese et al., "Generation and Detection of Coherent Terahertz Waves Using Two Photomixers," *Applied Physics Letters*, 1998; 73(26):3824-3826.

Wu et al., "Two-Dimensional Electro-Optic Imaging of THz Beams," *Appl. Phys. Lett.*, 1996; 69(8):1026-1028.

Yasui et al., "Terahertz Frequency Comb by Multifrequency-Heterodyning Photoconductive Detection for Hig-Accuracy, High Resolution Terahertz Spectroscopy," *Applied Physics Letters*, 2006; 88(241104):1-3.

\* cited by examiner

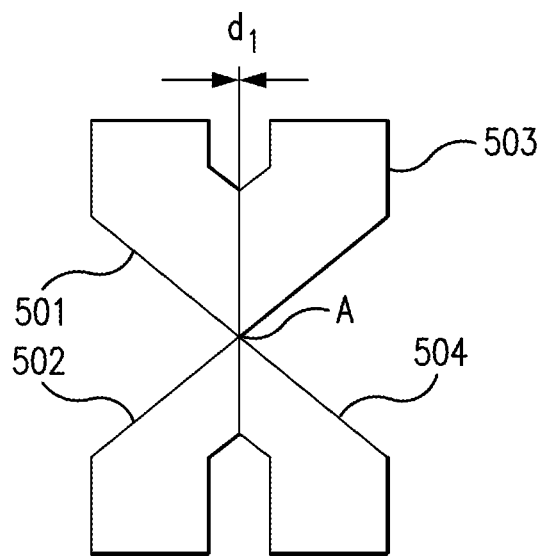
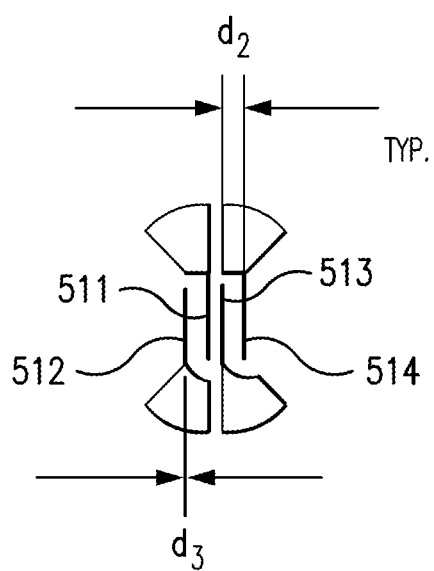
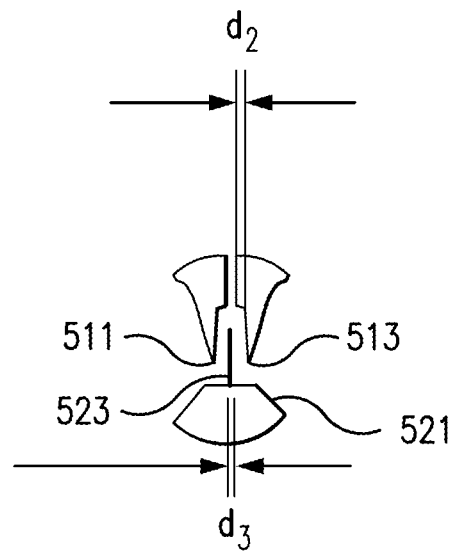
FIG. 2
FIG. 3
FIG. 4

TERAHERTZ FREQUENCY DOMAIN SPECTROMETER WITH A SINGLE PHOTOCONDUCTIVE ELEMENT FOR TERAHERTZ SIGNAL GENERATION AND DETECTION

This application claims the benefit of Provisional Application No. 61/790,973 filed Mar. 15, 2013, which is incorporated herein by reference in its entirety.

BACKGROUND OF THE INVENTION

1. Field of the Invention

The invention relates to microwave, millimeter wave and submillimeter wave spectroscopy systems and components and in particular to an apparatus and method for generating and detecting terahertz signals using a single photoconductive element.

2. Description of the Related Art

Terahertz devices and systems generally employ electromagnetic energy between 300 gigahertz (300 GHz) and 3 terahertz (3 THz), or wavelengths from 100 to 1000 microns (0.1 to 1.0 millimeters), which is also referred to as the submillimeter or far-infrared region of the electronmagnetic spectrum.

One important application of terahertz systems is terahertz spectroscopy. Terahertz spectroscopy presents many new instrumentation and measurement applications since certain compounds and objects can be identified and characterized by a frequency-dependent absorption, dispersion, and/or reflection of terahertz signals which pass through or are reflected from the compound or object.

One way of generating terahertz radiation is by photomixing two optical signals of different frequencies using an optical-heterodyne converter or photomixer. Typical photomixer devices include low-temperature-grown (LTG) GaAs semiconductor devices, which have been used to generate coherent radiation at frequencies tip to 5 THz. The spectroscopy system typically uses two single frequency tuneable lasers, such as diode lasers, to generate two optical laser beams which are directed at the surface of the photomixer. By photoconductive mixing of the two beams in the semiconductor material, a terahertz difference frequency between the two optical laser frequencies is generated. In particular, a first laser generates radiation at a first frequency and a second laser generates radiation at a second frequency. The difference frequency, equal to the difference between the first and the second laser frequencies, is swept by the user from microwave through terahertz frequencies by changing the temperature of one or both lasers. Other types of tuning mechanisms exist, such as distributed-Bragg-reflector diode lasers with multiple electrodes, grating-loaded external cavities, etc.

Conventionally, a terahertz transceiver has a transmitter, including a first photomixer device, and a receiver, including a second photomixer device. The first photomixer device is optically coupled to the first and the second light source, and a first radiative element or antenna is electrically coupled to the first photomixer device. In operation, the first antenna radiates a terahertz signal, generated by the first photomixer device at the difference frequency, toward a sample material. Terahertz radiation transmitted through, or reflected from, the sample material is directed to the receiver and is incident on a second antenna, which is electrically coupled to the second photomixer device. The second photomixer device is also optically coupled to the first and second light sources. The second antenna generates a time varying voltage proportional to the terahertz return signal. Under illumination by the first and second light sources, the second photomixer generates a homodyne downconverted current signal in response to the time varying voltage generated by the second antenna. The downconverted signal is a measurement of the absorption or reflection by the sample material at each terahertz frequency. This is useful, for example, when used in conjunction with computer processing to identify unknown samples by comparing measured results to a library of reference spectra. This apparatus may also be used to characterize the frequency response characteristics of passive or active components and devices such as waveguides, filters, amplifiers, mixers, diodes, and the like designed to work at terahertz frequencies.

Typically, THz spectroscopy systems employ lock-in detection techniques to improve signal to noise levels. These lock-in techniques involve, in the transmitter, modulating the amplitude of the photomixer current in the first photomixer device by either chopping the optical signal or modulating a bias voltage applied to the first photomixer device. It is, however, important that the second photomixer device in the receiver does not pick up the modulation directly, but only via the THz signal received from the sample material. If the modulation is detected directly by the second photomixer device, the signal from the sample material will be masked. For this reason, separate photomixer devices are used in the transmitter and the receiver, and the separate photomixer devices are located away from each other.

US 2012/0326039 describes using optical phase modulation as an alternative to modulating the amplitude of the photomixer current in the first photomixer device. By converting the phase modulation into an amplitude modulation via an interference pattern, it is possible to maintain a constant bias across the photomixer device in the transmitter without requiring the use of a chopper. In this way, the level of the THz signal is increased.

SUMMARY OF THE INVENTION

1. Objects of the Invention

It is another object of the present invention to provide a terahertz spectrometer having a reduced number of components. In particular, it is an object of the invention to provide a terahertz spectrometer having a single photoconductive element. In this way, the transmitter and the receiver can be mounted together more compactly.

It is an object of the present invention to provide an improved frequency domain terahertz spectrometer using two continuously tuneable semiconductor lasers with the phase of the optical beam applied to the photoconductive element being electronically modulated or adjustable.

It is still another object of the present invention to provide a self-contained, field portable terahertz spectrometer system in a highly compact configuration capable of identifying or imaging an object utilizing a laser with an electronically adjustable or controllable phase.

Some implementations may achieve fewer than all of the foregoing objects.

2. Features of the Invention

Briefly, and in general terms, the present disclosure provides an apparatus for analyzing, identifying or imaging a target, including a laser system which generates first and second laser beams having respective different frequencies. The first and second laser beams are directed along an optical path to a photoconductive element. An antenna structure is formed on the photoconductive element, the antenna structure having a first antenna for radiating electromagnetic radiation having a frequency dependent on the difference between the respective frequencies of the first and second laser beams and a second antenna for generating a detection signal. The laser system is arranged such that the first and second laser beams overlap in a region of a surface of the photoconductive element having at least part of the first and second antennas formed thereon.

The antenna structure may have interdigitated conductive fingers. A first conductive finger may be coupled to a first electrode forming part of the first antenna, a second conductive finger may be coupled to a second electrode forming part of the second antenna, and a third conductive finger may be coupled to a third electrode forming part of at least one of the first and second antennas. The laser region may be arranged such that the first and second laser beams overlap in the region of the surface of the photoconductive material including the interdigitated conductive fingers.

The third electrode may form part of the first antenna and a fourth finger may be coupled to a fourth electrode forming part of the second antenna. Alternatively, the third electrode may be common to the first and second antennas.

The third conductive finger may be disposed between the first and second conductive fingers.

The antenna structure may be in the form of a dual-dipole antenna.

A phase modulator may modulate the phase of one or both of the first and second laser beams. The phase modulator may be a lithium niobate modulator. The phase modulation of the CW signals by the phase modulator may result in a constructive or destructive interference of a THz beam and the overlapped first and second laser beams on the photoconductive element. A signal source may be coupled to the phase modulator to allow the first output beam to be swept in phase over 360 degrees. The frequency of the signal source may be selectable to allow the operator to analyze a specified frequency band of interest. The signal source coupled to the phase modulator may be swept in phase as the first output beam is swept in frequency.

A heterodyne detection system may be provided that includes a lock-in amplifier coupled to the detector, wherein the signal source coupled to the phase modulator is also coupled to the lock-in amplifier.

The first and second laser beams may be generated by first and second lasers disposed in a first housing, and the photoconductive element may be disposed in a second housing separate from and spaced apart from the first housing, wherein the first housing and the second housing are coupled by an optical fiber. A processor may be disposed in the first housing for determining a characteristic of the target based upon the reflection characteristics of the target in a frequency range in the 100 MHz to over 2 THz frequency band.

The photoconductive element may be a low temperature grown GaAs photoconductive switch.

Some implementations or embodiments may incorporate or implement fewer of the aspects or features noted in the foregoing summaries.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein:

FIG. 2 schematically shows a dual-dipole antenna structure formed on a photoconductive element forming part of the frequency domain terahertz spectrometer illustrated in FIG. 1;

FIG. 3 schematically shows in more detail an illuminated portion A of the antenna structure illustrated in FIG. 2;

FIG. 4 schematically shows in more detail an alternative illuminated portion A of the antenna structure illustrated in FIG. 2;

Figure 1:
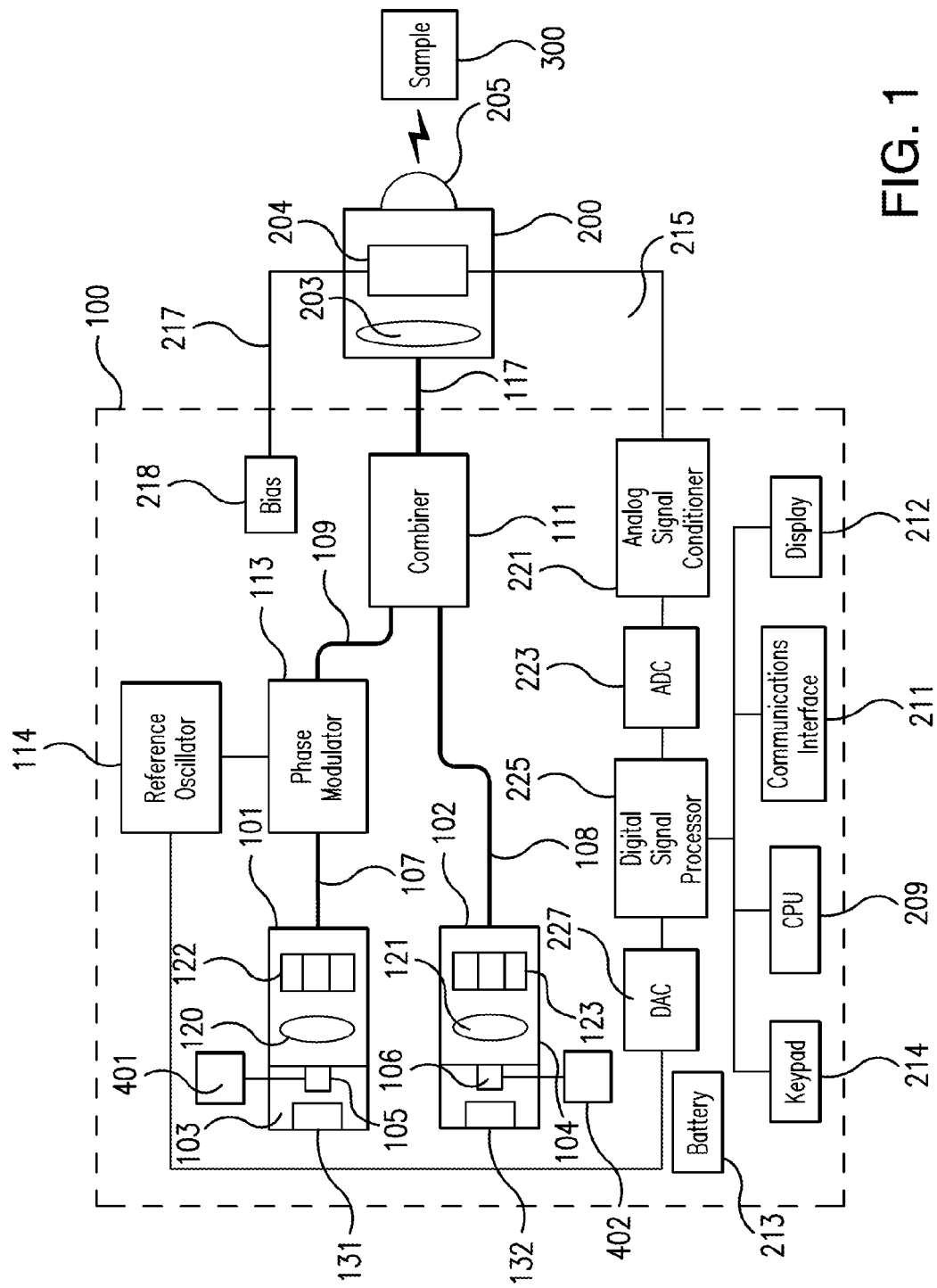
FIG. 1 is a block diagram schematically showing the main components of a frequency domain terahertz spectrometer according to the present disclosure.

The novel features and characteristics of the disclosure are set forth in the appended claims.

DETAILED DESCRIPTION OF THE PREFERRED EMBODIMENT

Details of the present disclosure will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As noted above, in the frequency domain technique for terahertz spectroscopy, continuous-wave (CW) THz radiation is produced through photomixing of the combined output of two single-frequency diode lasers in a low temperature grown GaAs photomixer (also referred to as a photoconductive switch or PCS). The wavelength of one (or both) of the lasers is tuned by temperature adjustment of the laser to coarsely vary the THz output frequency, which may therefore be swept over one or more frequency bands of interest for characterizing the target or sample material.

In FIG. 1, there is depicted a housing 100 incorporating the optical and electro-optical components suited for use as a subassembly in conjunction with a coupled spectrometer head 200. A fiber optic cable 117, a first electrical cable 215 and a second electrical cable 217 couple the housing 100 to the spectrometer head 200. It will be appreciated that the fiber optic cable 117 and the first and second electrical cables 215,217 can be bundled together in a common cable packaging so that a single cable interconnects the housing 100 and the spectrometer head 200.

A silicon lens 205 on the exterior of the housing 200 enables the terahertz radiation to be focused or directed to a sample material 300 by the user, and collects terahertz radiation reflected from the sample material 300. It is noted that additional optical elements including but not limited to lenses, focusing mirrors, parabolic reflectors, sub-reflectors, beam-splitters/combiners, and beam-shaping optics (not shown for clarity) may also be employed to provide focusing or manipulation of the radiated terahertz beams, as the particular measurement situation requires.

In some embodiments, the housing 100 is sized and designed to be lightweight and portable, and worn or supported by the user during operation. Inside the housing 100 are mounted two laser subassemblies 101 and 102 including lasers 105 and 106, respectively, which are preferably two distributed feedback (DFB) or distributed Bragg reflector (DBR) semiconductor laser diodes with single-longitudinal-mode and single spatial-mode operation over a range of wavelengths around 783 nm. Suitable lasers are available from various vendors (for example, Eagleyard Photonics GmbH of Berlin, Germany, or Photodigm, Inc. of Richardson, Tex.). In some embodiments it would also be possible to utilize one or more packaged external-cavity tuneable semiconductor lasers such as are available from Emcore Corporation, of Newark, Calif., such as disclosed in U.S. patent application Ser. No. 12/722,825, filed Mar. 12, 2010 (the whole content of which is hereby incorporated by reference). The diode laser packaging permits co-collimation of the laser beams to a very high degree of precision, and the design allows very precise frequency control of the lasers by temperature and/or electronic tuning, and monitoring the laser output through digital signal processing, to achieve more accurate control over the laser output beam frequencies.

In one embodiment, the laser diode chips 105 and 106 are mounted on independent Peltier thermoelectric coolers (TECs) 103 and 104. The center wavelengths of the lasers are nominally 783 nm at 25° C., but the lasing wavelengths may be coarsely temperature-tuned using the respective TECs 103, 104 with a tuning coefficient of approximately 0.1 nm per ° C. Therefore, a 50 degree C. temperature range of operation from −10 degrees C. to +40 degrees C. will yield a frequency range of approximately 5 nm. For the purposes of illustration only, if the DFB lasers are selected such that their center wavelengths at 25 degrees C. are at 782 nm and 784 nm, respectively, then a thermal tuning range of −10 degrees C. to +40 degrees C. on each laser chip will permit generation of offset wavelengths 0 nm to approximately 7 nm, corresponding to a range of offset frequencies from 0 Hz to 3.4 THz. The thermal mass on the controlled surface of the TECs 103, 104 is such that it allows rapid frequency tuning. In the case of DBR laser diode chips, the Bragg-reflection section of each laser may be adjusted electronically to vary the laser frequency. Wider offset frequency ranges may also be possible by employing wider temperature excursion, or by using DBR or external cavity lasers.

Current sources 401, 402 inject current into the lasers 105, 106 respectively so that the lasers 105, 106 output optical signals. The amplitude of the optical signals output by the lasers 105, 106 are monitored using respective back photodiodes 131, 132, and the amplitude of the optical signals output by the lasers 105, 106 is maintained constant by a feedback loop (not shown) to the current sources 401, 402. The output beam from each laser 105, 106 is collimated with an aspheric lens 120, 121 respectively, mounted on a precision lens-mount with sub-micron adjustment capability (see, e.g. U.S. Pat. No. 7,126,078). After passing through a respective lens 120, 121, the laser output beams are directed through a respective optical isolator 122 and 123, to prevent feedback into the laser, and to couple the output beam to pigtail optical fibers 107 and 108, respectively.

In the embodiment depicted in the present disclosure, the output beam from laser 105 is directed along the optical fiber 107, or first path, to a phase control element such as a phase modulator 113. The phase modulator 113 may be a lithium niobate device, such as those manufactured by Photline Technologies of Besancon, France. A reference oscillator 114 is connected to the phase modulator 113 for sweeping or precisely incrementing or decrementing the phase by a periodic or other type of signal. The phase modulator 113 allows the user to sweep the phase automatically (by pre-programmed software) or to manually adjust the phase of the laser output beam in a highly precise manner, thereby also adjusting the phase of the emitted CW terahertz beam. In some embodiments, the signal applied to the phase modulator 113 is a periodic 6 kHz signal, or more generally, a periodic signal that is swept at a rate at least twice as fast as the rate at which the laser frequency is swept.

The output of the phase modulator 113 is then directed along a fiber 109 to a waveguide coupler or beam combiner 111. The optical beam output by laser 106 is coupled into a fiber 108, which directs the output beam to the beam combiner 111, which combines the optical beam output by the phase modulator 113 with the optical beam output by the laser 106. The output of beam combiner 111 is then coupled into fiber 117, which exits the module 100 and is subsequently directed to the spectrometer head 200.

The optical propagation path downstream of the lasers and throughout the unit 100 may be an appropriate single-mode polarization-maintaining optical fiber (PMF) or free space. As can be appreciated, the basic topology depicted in FIG. 1 uses fiber optical implementation which readily illustrates the various optical paths.

In source head 200, the composite output beam of the two distinct laser sources is then applied to a lens 203 which focuses the beam to a spot of approximately ten microns in diameter on the surface of a low temperature grown (LTG) gallium arsenide (GaAs) photoconductive element 204. The two optical beams are combined or photomixed in the photoconductive element 204. Other types of photoconductive elements may alternatively be used. First and second antennas are formed on the photoconductive element 204, and a constant DC electrical bias from a bias signal generator 218 is coupled to the first antenna by cable 217.

The terahertz variation in the intensity of the mixing or difference signal between the two laser frequencies, often referred to as the "heterodyne laser signal", produces a terahertz modulation of the conductance in the material of the photoconductive element, which in turn produces a terahertz current flow in the first antenna patterned on the surface of the photoconductive element 204. This current in the first antenna produces an electromagnetic field, i.e. terahertz radiation, propagating into the surrounding space and having a frequency range from typically 100 MHz to over 2 THz, depending on the difference frequency of the two laser sources. The terahertz radiation so produced is emitted from the photoconductive element 204 and then collimated and collected by a silicon lens 205, preferably a hemispherically shaped structure approximately two to three centimeters in diameter. Additional lenses (not shown), composed of TEFLON™ or other suitable materials may be placed downstream of the lens 205 to collimate the RF beams into an output terahertz beam. Beam-shaping mirrors may also be used in lieu of or in addition to the silicon lens 205 in the spectrometer head 201.

In an embodiment, the outgoing terahertz radiation beam from the photoconductive element 204 is relatively low power, about 1 to 10 microwatts. The target sample 300 is typically positioned relatively close to the spectrometer head 200, and reflects a portion of the terahertz radiation back in the direction of the spectrometer head 200.

A terahertz return signal from the target sample 300 is captured by the silicon lens 205 in the spectrometer head 200, which focuses the return terahertz beam to the second antenna patterned on the surface of photoconductive element 204, which also acts as a terahertz radiation detector. In embodiments contemplated by the present disclosure, the terahertz variation in the intensity of the mixing or difference signal between the two laser frequencies, in combination with the terahertz modulation of the conductance in the material of the photoconductive element 204 as a result of the terahertz current flow in the second antenna from the received terahertz signal from the sample, results in a heterodyning and down conversion of the received terahertz signal to a baseband frequency equal to the frequency of the reference oscillator 114. A synchronous detection circuit makes use of the reference oscillator 114 signal applied to the phase modulator 113, and thereby to the signal applied to the photoconductive element 204, as a reference for the synchronous detection process.

FIG. 2 schematically shows the antenna structure formed on the photoconductive element 204. As shown, the antenna structure incorporates both the first antenna and the second antenna into a single device. In particular, the first antenna has a first electrode 501 and a second electrode 502. The first electrode 501 is formed by a first conductive strip which generally extends along a longitudinal axis and tapers at one end to form a first conductive finger 511, shown magnified in FIG. 3. The second electrode 502 is formed by a second conductive strip which also generally runs along the longitudinal axis and tapers the end proximate the first electrode to form a second conductive finger 512, also shown in FIG. 3. As shown in FIG. 3, the first conductive finger 511 and second conductive fingers 512 run parallel to each other, but no direct contact is made between the first electrode 501 and the second electrode 502. Accordingly, when the bias signal is applied to the first electrode 501, the amount of current flowing in the first antenna is dependent on the photoconductivity of the material of the photoconductive element 204.

The second antenna is formed by a third electrode 503 and a fourth electrode 504. The first electrode is formed by a third conductive strip generally extends parallel to the first electrode 501, and which tapers at the end adjacent the tapered end of the first electrode 501 to form a third conductive finger 513. The fourth electrode 504 is formed by a fourth conductive strip which is generally aligned with the third electrode 503, and which tapers at the end proximate the third electrode 503 to form a fourth conductive finger 514. As shown in FIG. 3, the third conductive finger 513 and the fourth conductive finger 514 run parallel to each other, but there is no direct contact between the third electrode 503 and the fourth electrode 504.

As shown in FIG. 2, the tapered portions of the first electrode 501 and the second electrode 502 are separated by a distance $d_1$, which in this embodiment is 0.0016 mm. As shown in FIG. 3, the first conductive finger 511 is separated from the second conductive finger 512 by a distance $d_2$, which is preferably less than 2 μm. In this embodiment, $d_2$ is also 0.0016 mm. Similarly, the first conductive finger 511 is separated from the third conductive finger 512 by the distance $d_2$, and the third conductive finger 513 is separated from the fourth conductive finger 514 by the distance $d_2$. The first to fourth conductive fingers 511-514 each have a thickness $d_3$, which is preferably less than 0.5 μm. In this embodiment, $d_3$ is 0.00040 mm.

In an alternative embodiment, illustrated in FIG. 4, the first and second antennas share a common electrode 521, which replace the second electrode 502 and the fourth electrode 504. As shown in FIG. 4, the common electrode 521 tapers to a conductive finger 523 which extends between the first conductive finger 511 and the third conductive finger 513. In particular, the conductive finger 523 lies midway between the first conductive finger 511 and the third conductive finger 513, and is separated from each of the first conductive finger 511 and the third conductive finger 513 by the distance $d_2$. The width of the conductive finger 523 is $d_3$.

Returning to FIG. 1, a signal resulting generated in the second antenna is coupled by the electrical cable 215 to an analog signal conditioner 221. The analog electrical signal output by the analog signal conditioner 221 is converted into a digital signal by an analog-to-digital converter (ADC) 223, and the resultant digital signal is input to a digital signal processor 225. As will be discussed in more detail hereinafter, the digital signal processor 225 outputs, via a digital-to-analog converter 227, a control signal to the reference oscillator 114, and determines magnitude and phase values for the received terahertz signal detected by the second antenna, and forwards the determined magnitude and phase values to a central processing unit (CPU) 209. The terahertz spectrometer may incorporate software for automatically determining the identity or composition of the target sample based on the determined magnitude values at a plurality of terahertz frequencies. The terahertz spectrometer may further incorporate other electronic elements for printing or displaying the results so that the analysis, identification, or image information is readily available to the user. As shown in FIG. 1, the terahertz spectrometer may incorporate a communications interface (which may be a wireless RF transceiver for communicating the results to an external user or network element) 211, a display 212, and a keypad 214 as examples of elements providing user or operator interface. A battery 213, or other self-contained power source, may be provided to make the unit field portable.

Figure 5:
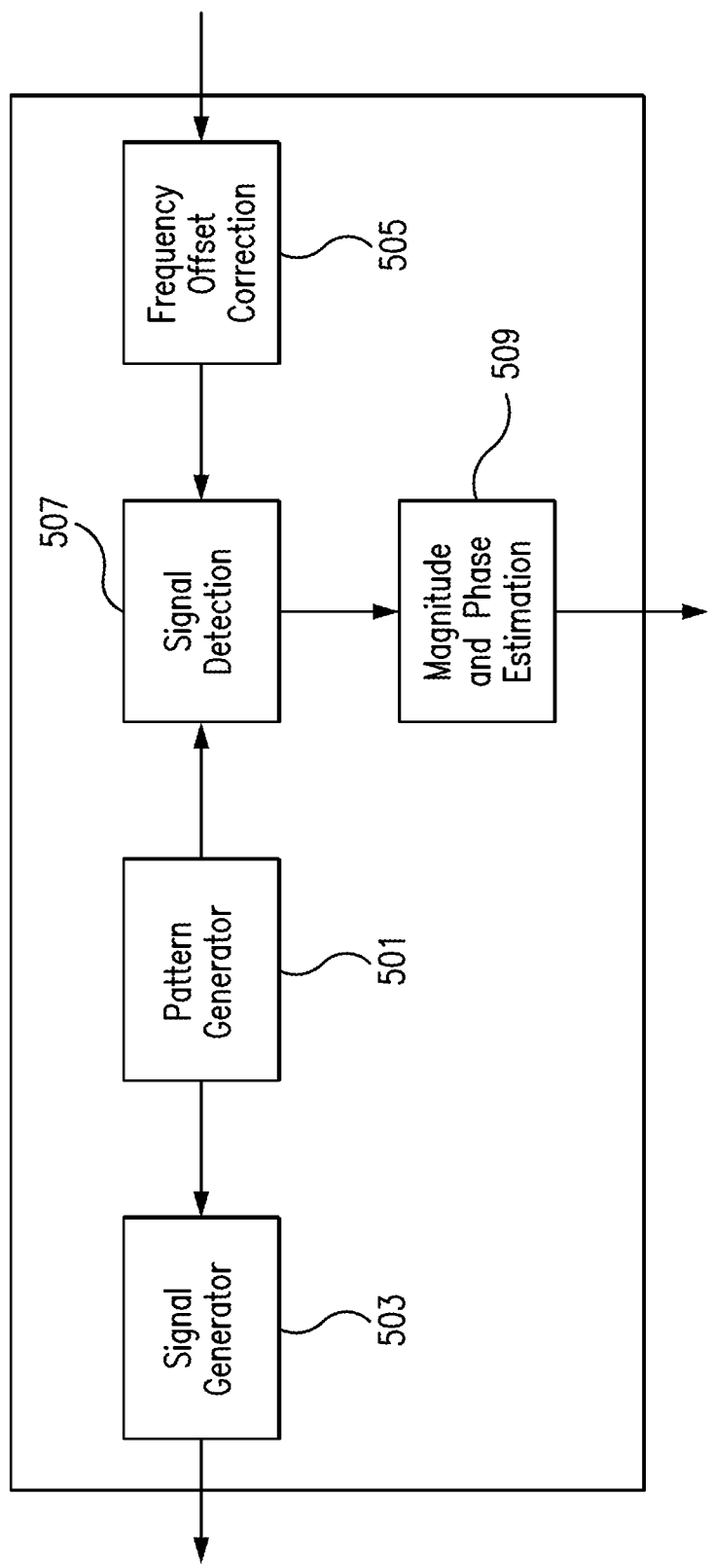
FIG. 5 is a block diagram schematically showing operation of the digital signal processing.
Figure 6:
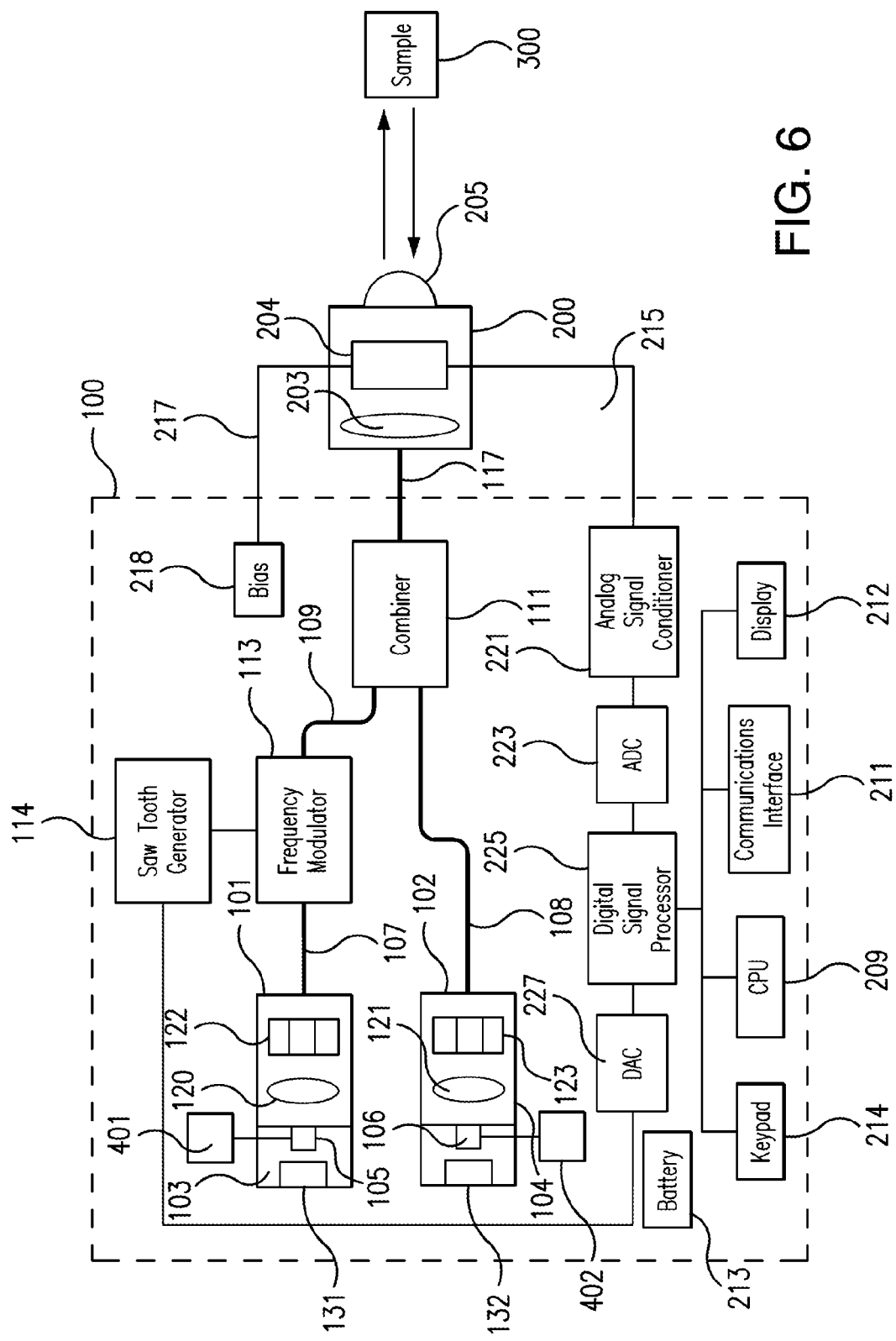
FIG. 6 is a block diagram schematically showing the main components of a frequency domain terahertz spectrometer according to another embodiment in which the phase modulator is omitted, and in its place a beam chopper is interposed between the source head and the sample or target under test.
Figure 7:
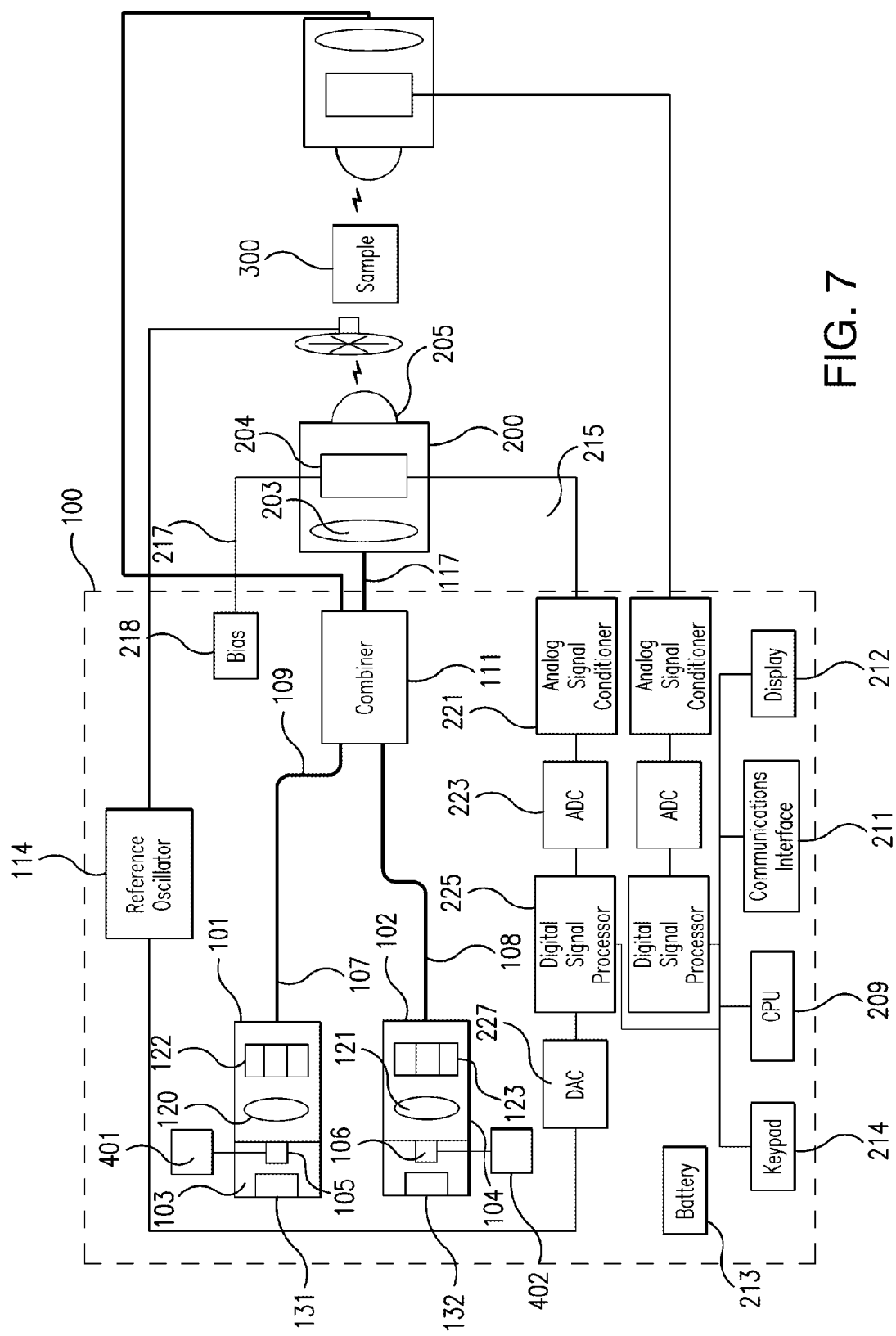
FIG. 7 is a block diagram schematically showing the main components of a frequency domain terahertz spectrometer of FIG. 1 according to another embodiment in which a detector head is placed behind the sample or target to make simultaneous, phase coherent reflection and transmission measurements.
Figure 8:
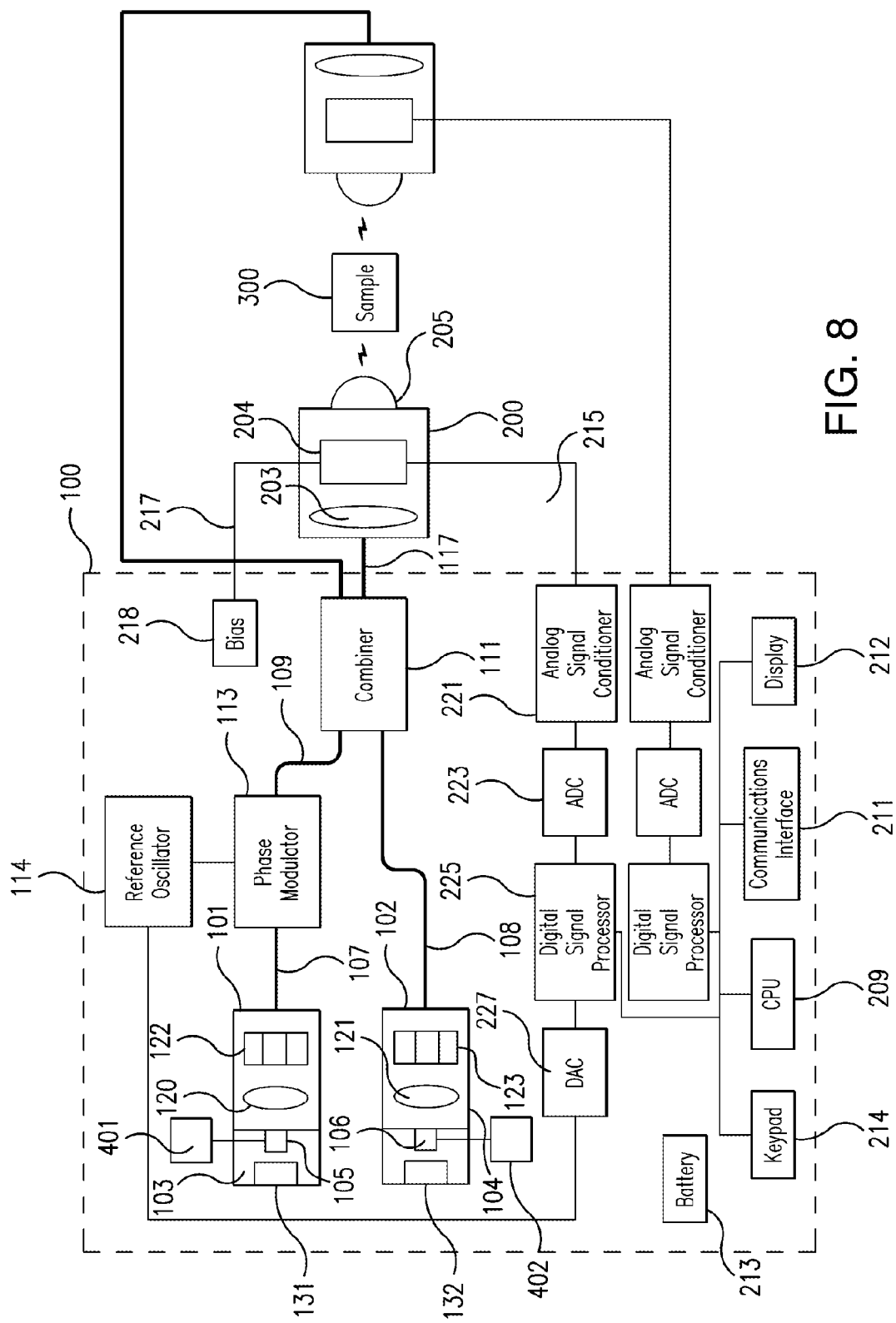
FIG. 8 is a block diagram schematically showing the main components of an apparatus according to another embodiment of the present disclosure, a variation of the apparatus of FIG. 1, which represents a THz Frequency Domain Reflectometer (TFDR). The TFDR works in a manner similar to an optical Frequency Domain Reflectometer (OFDR), but in the THz domain. A saw tooth generator 114 applies a signal to the frequency modulator 113. The frequency is changed quickly enough such that when the THz signal is emitted from the head 200, reflects off the sample, returns to the head 200 and the detector, and mixes with the outgoing signal, it is mixing not with the same frequency, but at a slightly offset frequency. By examining the spectrum of the signal on the receiver and knowing the frequency ramp rate, one can tell the time delay for the THz return signal for each target pixel being scanned. By suitably scanning a specific two dimensional region of the target with the THz beam (in one or more swept frequency ranges), and recording the time delay (and therefore distance from the radiation source head to the surface of the target), and reconstructing the two dimensional surface region of the target, it is feasible to perform 2D or 3D imaging of a target with a THz CW system. Background and technical details of various arrangements and methods for performing imaging using THz systems are described in US Published Patent Application No. 20120075477; 20110068268; 20100171835; 20090091820; 20080251720; 20080251720; 20080179519; and U.S. Pat. Nos. 6,828,558; 6,957,099; 7,174,037; 7,335,883; 7,693,571; and 7,804,069, all of which are hereby incorporated by reference.

The operation of the digital signal processor 225 will now be described in more detail with reference to FIG. 5. As shown, the digital signal generator 225 includes a pattern generator 501. In this embodiment, the pattern generator 501 outputs a first signal, corresponding to a 500 kbps pseudo random pattern (PN) that is exclusive OR'd with a variable rate alternating pattern of 1's and 0's, to a signal generator 503, which performs digital quadrature modulation to produce a 550 kHz wide pass band signal ($S_{mod}(t)$) centered at an intermediate frequency of 10.7 MHz. This wide pass band signal is converted to an analog signal by the DAC 227, and input to the reference oscillator 114 in order phase modulate, using the phase modulator 113, the output of the laser 105. The frequency of the laser 105 is $f_{LDB}$, and the phase modulator outputs a modulated signal $S'_{LDB}(t)=A*COS(2*\pi*f_{LDB}*t+S_{mod}(t))$.

The modulated signal $S'_{LDB}(t)$ is combined with the CW output of the laser 106 which has a frequency centered at $f_{LDA}$. The combined optical signal is presented to the photoconductive element 204 to produce a THz signal, $S_{THz\_tx}(t)=A*COS(2*\pi*(\Delta f)*t+S_{mod}(t))$, where $\Delta f$ is the absolute value of the difference between $f_{LDA}$ and $f_{LDB}$. The THz signal, $S_{THz\_tx}(t)$, propagates a distance D to the target sample 300, reflects off of the target sample 300 and returns to the photoconductive element 204 at some time $\Delta t$ after it was produced. The reflected signal $(S_{THz\_tx}(\Delta t)=A*COS(2*\pi*(\Delta f)*\Delta t+S_{mod}(\Delta t)))$ gets mixed with the current signal $S_{THz\_tx}(t)$, producing a signal $A*S_{mod}(\Delta t)$ (plus noise) at the second antenna.

The signal at the second antenna passes through the analog signal conditioner 221, which reduces noise, and is converted to a digital signal by the ADC 223. The digital signal output by the ADC 223 is input to the digital signal processor 225, and passes through a frequency offset correction module 505 which adjusts the input signal to take account of the variation in the wavelength of one or both of the lasers 105, 106 over time. The signal is then input to a signal detection module 507 together with a second signal from the pattern generator 501, corresponding to the 500 kbps pseudo random pattern (PN). The signal detection module 507 performs digital quadrature demodulation to produce I and Q base band signals that are correlated against the 500 kbps pseudo random pattern (PN).

The I and Q base band signals are then input to a magnitude and phase estimation module 509, which produces a receive signal magnitude and phase offset values. In particular, timing information, that can be used for determining the distance of the target sample 300 in the THz scan and other purposes, is recovered by measuring the phase difference between sign of the autocorrelation value with the sign of the input 1's and 0's pattern. If the frequency is being ramped during a measurement, distance can also be obtained from the offset error value found during the receive signal frequency correction.

In one embodiment, the frequency of one of the lasers, and consequentially the radiative terahertz frequency, is swept or tuned through a series of frequencies, or through a sequence of distinct specific frequency bands. The return terahertz signal Sout is collected by the spectrometer head 200 and transferred to digital signal processor 225 for data collection and analysis at each specific frequency of interest. In this way, the absorption or reflection spectrum of the sample under test can be collected with high resolution and high signal-to-noise ratio since all of the terahertz energy is centered in a single tone and the lock-in amplifier limits the noise bandwidth. This, incidentally, is a major advantage of the frequency domain technique compared to time-domain techniques in which the terahertz energy is spread over many frequencies. In some embodiments, the tuning and terahertz emission may be adapted to a specific sequence or set of frequency bands having spectral absorption peaks corresponding to the unique spectral signature of a particular material of concern. Thus, the frequency sweeping time may be minimized if the user's application was solely the question: "Is compound X present in the sample?", since the processor and software in the spectrometer may be pre-programmed to only generate, sweep, record and analyze the terahertz frequency bands associated with the spectral signature of a particular material of concern.

In summary, certain aspects of the present disclosure may provide a compact frequency domain terahertz coherent spectrometer with either continuous tuning, or discrete tuning within certain identified frequency bands greater than 100 GHz. Such construction may employ highly compact photonic integration techniques, and room-temperature coherent THz detection. Advantageously, such devices may offer rapid identification of chemical, biological and explosive materials in both the solid-phase and the gas-phase at standard atmospheric pressure. Some embodiments may utilize a highly integrated photonic assembly employing semiconductor diode lasers employing no moving parts, so that it is inherently rugged and well-suited to field-deployable applications. The frequency-shifted optical beams are incident on the source PCS (or alternatively, in other embodiments, the detector PCS, or both), and provides a means to effect extremely high-resolution spectroscopy. Typical thermal tuning resolution and accuracy of the source lasers may perform coarse tuning over a wavelength range up to 7 nm, in intervals or step sizes of smaller than 0.0001 nm.

Of course, various modifications and improvements of the present disclosure may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

It will be understood that each of the elements described above, or two or more together, also may find a useful application in other types of constructions differing from the types described above. In particular, certain configurations presented according to particular aspects of the present invention have been shown and described as discrete elements, i.e., lasers, splitters, combiners, mirrors, lenses, shifters, fiber optical cable, etc. Those skilled in the art will readily appreciate that many or all of these individual, discrete components may be fabricated and/or packaged into integrated elements. By way of particular example, the use of integrated waveguides and associated structures is envisioned for the described structures and arrangements. Alternatively, the discrete elements, i.e., lasers, splitters, combiners, mirrors, lenses, shifters, etc. may also be individually-packaged in modules with optical fiber interconnects to achieve the same topology and functionality.

While the present disclosure illustrates and describes a terahertz transceiver or spectrometer system, it is not intended to be limited to the details shown, since various modifications and structural changes may be made without departing in any way from the spirit of the present invention.

The foregoing described embodiments depict different components contained within, or connected with, different other components. It is to be understood that such depicted arrangements or architectures are merely exemplary, and that in fact many other arrangements or architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of specific structures, architectures or intermedial components. Likewise, any two components so associated can also be viewed as being "operably connected" or "operably coupled" to each other to achieve the desired functionality.

While particular embodiments of the present invention have been shown and described, it will be understood by those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," "comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Without further analysis, from the foregoing others can, by applying current knowledge, readily adapt the disclosed technology for various applications. Such adaptations should and are intended to be comprehended within the meaning and range of equivalence of the following claims.

The invention claimed is:

1. An apparatus for analyzing, identifying or imaging a target, the apparatus comprising:
   a laser system operable to generate first and second laser beams having respective different frequencies, and to combine the first and second laser beams in an optical path;
   a photoconductive element provided in the optical path exposed to the combined first and second laser beams to emit electromagnetic radiation having a difference frequency dependent on a difference between said respective different frequencies of the first and second laser beams such that the electromagnetic radiation at the difference frequency is incident on the target which produces a return electromagnetic radiation that is co-incident on the photoconductive element with the combined first and second laser beams and detected by the photoconductive element to produce a detection signal such that a single photoconductive element produces (i) the difference frequency that is incident on the target as well as (ii) the detection signal responsive to the return electromagnetic radiation; and
   a processor for processing the detection signal to identify at least one characteristic of the target.

2. The apparatus according to claim 1, further comprising:
   an antenna structure formed on the photoconductive element including a first antenna exposed to the combined first and second laser beams for emitting the electromagnetic radiation at the difference frequency and a second antenna, and wherein a laser region of the antenna structure includes interdigitated conductive fingers comprising:
   a first conductive finger coupled to a first electrode forming part of the first antenna;
   a second conductive finger coupled to a second electrode forming part of the second antenna; and
   a third conductive finger coupled to a third electrode forming part of at least one of the first and second antennas.

3. The apparatus according to claim 2, wherein the laser region is arranged such that the first and second laser beams overlap at the surface of the photoconductive element including the interdigitated conductive fingers.

4. The apparatus according to claim 2, wherein the third electrode forms part of the first antenna and the interdigitated fingers further comprise a fourth finger coupled to a fourth electrode forming part of the second antenna.

5. The apparatus according to claim 2, wherein the third electrode is common to the first and second antennas.

6. The apparatus according to claim 5, wherein the third conductive finger is between the first and second conductive fingers.

7. The apparatus according to claim 2, wherein the separation of adjacent ones of the interdigitated conductive fingers is less than 21.1 m.

8. The apparatus according to claim 7, wherein the width of each conductive finger is less than 0.5 mm.

9. The apparatus according to claim 2, wherein the first and second antennas form a dual-dipole antenna structure.

10. The apparatus according to claim 1, wherein the laser system comprises a modulator for modulating the phase of at least one of the first and second laser beams.

11. The apparatus according to claim 10, wherein the processor is arranged to generate a data pattern for controlling said phase modulation, wherein the processor is operable to perform synchronous detection of the detection signal using said data pattern.

12. The apparatus according to claim 11, wherein the processor comprises a signal generator operable to perform quadrature modulation using said data pattern, and a signal detector operable to perform quadrature demodulation of the detection signal to generate first and second baseband signals.

13. The apparatus according to claim 12, wherein the processor is operable to process said first and second baseband signals to determine magnitude and phase values for the detection signal.

14. The apparatus according to claim 1 wherein the electromagnetic radiation at the difference frequency is focused on the target by at least a given lens and the return electromagnetic radiation passes through the given lens in a reverse direction returning to the photoconductive element.

15. The apparatus according to claim 1 further comprising:
a frequency controller for sweeping the frequency of one of the first and second lasers relative to the other one of the first and second lasers to produce the difference frequency such that the return electromagnetic radiation presents a return frequency at the photoconductive element that is offset from the difference frequency by a time delay; and
said processor is configured to identify the characteristic based on the offset frequency and the time delay.

16. A method for analyzing, identifying or imaging a target, the method comprising:
generating first and second laser beams having respective different frequencies;
combining the first and second laser beams in an optical path;
directing the combined first and second laser beams along the optical path to a photoconductive element such that the photoconductive element emits electromagnetic radiation having a difference frequency corresponding to a difference between said respective different frequencies of the first and second laser beams, and the electromagnetic radiation at the difference frequency is incident on the target which produces a return electromagnetic radiation that is co-incident on the photoconductive element with the combined first and second laser beams and detected by the photoconductive element to produce a detection signal such that a single photoconductive element produces (i) the difference frequency that is incident on the target as well as (ii) the detection signal responsive to the return electromagnetic radiation; and
processing the detection signal to identify at least one characteristic of the target.

17. The method according to claim 16, further comprising:
forming an antenna structure formed on the photoconductive element including a first antenna exposed to the combined first and second laser beams for emitting the electromagnetic radiation at the difference frequency and a second antenna, and to include a second antenna such that
a first conductive finger is coupled to a first electrode forming part of the first antenna;
a second conductive finger is coupled to a second electrode forming part of the second antenna; and
a third conductive finger is coupled to a third electrode forming part of at least one of the first and second antennas and the first, second and third conductive fingers are interdigitated.

18. The method according to claim 17, wherein the first and second antennas form a dual-dipole antenna structure.

19. The method according to claim 17, further comprising modulating the phase of at least one of the first and second laser beams.

20. The method according to claim 19, wherein said phase modulation is in accordance with a data pattern, and wherein the method further comprises performing synchronous detection of the detection signal using said data pattern.

21. The method according to claim 20, further comprising performing quadrature modulation using said data pattern to generate a drive signal for said modulation, and performing quadrature demodulation of the detection signal to generate first and second baseband signals.

22. The method according to claim 21, further comprising processing said first and second baseband signals to determine magnitude and phase values for the detection signal.

23. The method according to claim 16 including focusing the electromagnetic radiation at the difference frequency on the target using at least a given lens and passing the return electromagnetic radiation through the given lens in a reverse direction returning to the photoconductive element.

24. The method according to claim 16 further comprising:
sweeping the frequency of one of the first and second lasers relative to the other one of the first and second lasers to produce the difference frequency such that the return electromagnetic radiation presents a return frequency at the photoconductive element that is offset from the difference frequency by a time delay; and
identifying the characteristic based on the offset frequency and the time delay.

* * * * *